United States Patent
Clifton et al.

(10) Patent No.: US 11,154,537 B2
(45) Date of Patent: Oct. 26, 2021

(54) METHOD OF TREATMENT FOR KETAMINE INFUSION

(71) Applicant: Kalypso TC LLC, San Antonio, TX (US)

(72) Inventors: John Bryan Clifton, San Antonio, TX (US); J Cannon Clifton, San Antonio, TX (US); Mark Alan Moran, San Antonio, TX (US); Scott Patrick Worrich, San Antonio, TX (US)

(73) Assignee: Eleusis Therapeutics US, Inc., New York, NY (US)

( * ) Notice: Subject to any disclaimer, the term of this patent is extended or adjusted under 35 U.S.C. 154(b) by 0 days.

(21) Appl. No.: 16/101,217

(22) Filed: Aug. 10, 2018

(65) Prior Publication Data

US 2020/0046683 A1    Feb. 13, 2020

(51) Int. Cl.

| | |
|---|---|
| *A61K 31/4178* | (2006.01) |
| *A61K 31/135* | (2006.01) |
| *A61K 45/06* | (2006.01) |
| *A61K 9/00* | (2006.01) |
| *A61P 25/24* | (2006.01) |
| *A61K 31/4045* | (2006.01) |
| *A61K 31/5513* | (2006.01) |
| *A61K 31/407* | (2006.01) |

(52) U.S. Cl.
CPC ........ *A61K 31/4178* (2013.01); *A61K 9/0019* (2013.01); *A61K 31/135* (2013.01); *A61K 45/06* (2013.01); *A61P 25/24* (2018.01); *A61K 31/407* (2013.01); *A61K 31/4045* (2013.01); *A61K 31/5513* (2013.01); *A61K 2300/00* (2013.01)

(58) Field of Classification Search
CPC .............. A61K 31/4178; A61K 9/0019; A61K 31/135; A61K 45/06; A61K 31/4045; A61K 31/407; A61K 31/5513; A61K 2300/00; A61P 25/24
See application file for complete search history.

(56) References Cited

U.S. PATENT DOCUMENTS

| | | |
|---|---|---|
| 5,543,434 A | 8/1996 | Weg |
| 5,989,582 A | 10/1999 | Weg |
| 6,248,789 B1 | 6/2001 | Weg |
| 8,785,500 B2 | 7/2014 | Charney et al. |
| 9,592,207 B2 | 3/2017 | Charney et al. |
| 10,172,810 B2 | 1/2019 | McCarty |
| 2004/0138298 A1 | 7/2004 | Mermelstein et al. |
| 2016/0220513 A1 | 8/2016 | Hashimoto |
| 2017/0095429 A1 | 4/2017 | Erickson et al. |
| 2018/0177797 A1 | 6/2018 | Berdahl et al. |
| 2018/0271877 A1 | 9/2018 | Berdahl et al. |
| 2019/0117591 A1 | 4/2019 | Basstanie et al. |
| 2020/0121619 A1 | 4/2020 | Rey |

OTHER PUBLICATIONS

Gupta et al (Year: 2014).*
Murrough et al (Year: 2013).*
Vozoris et al (Year: 2013).*
Ford et al (Year: 2015).*
Berman et al., Antidepressant effects of ketamine in depressed patients, Biol. Psychiatry, 47:351-354, 2000.
Rush et al., Research issues in the study of difficult-to-treat depression, Biol. Psychiatry, 53:743-753, 2003.
Receipt of Jun. 1, 2016, for payment by a patient regarding a treatment performed on a patient. The treatment consisted of an infusion of ketamine and atavan, which was a precursor treatment to the treatment claimed in the present application.

* cited by examiner

*Primary Examiner* — Jeffrey S Lundgren
*Assistant Examiner* — Ibrahim D Bori
(74) *Attorney, Agent, or Firm* — Tobin Hobbs

(57) ABSTRACT

Methods for treatment for patients having depression and/or pain are contemplated as including an administration of first preparation comprising an antiemetic agent, preferably ondansetron, followed by a second preparation of a synergistic combination of ketamine and a benzodiazepine, preferably lorazepam, administered via a continuous intravenous infusion. Such methods may be seen to better alleviate depression and pain symptoms, and may result in reduced need for other medications.

30 Claims, No Drawings

METHOD OF TREATMENT FOR KETAMINE INFUSION

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates generally to the field of ketamine therapy. More particularly, the present disclosure relates to the treatment of various conditions via administration of intravenous infusions containing ketamine and a benzodiazepine.

2. Related Art

Ketamine is a pharmaceutical agent used in medical settings for its analgesic (pain relief/prevention), sedative (reduction of irritation/agitation), and amnesiac (prevention of the formation of memories) properties. Together, all three of these properties are important in the induction and maintenance of anesthesia for the performance of medical procedures. For example, ketamine is widely used in the induction of maintenance of general anesthesia. Ketamine is also used widely used as a dissociative anesthetic in the practice of emergency medicine, as its dissociative (rather than depressive) effect at particular dosages may permit effective sedation in patients in who have suffered traumatic bodily injury and are in a condition of hypovolemic shock.

As used herein, the term "ketamine" will be understood to interchangeably refer to ketamine in all of its forms, including but not limited to its racemic form and all enantiomeric proportions of esketamine (S-ketamine or S-(+)-ketamine) and arketamine (R-ketamine or R-(−)-ketamine), including pure estakine and arketamine, any prodrugs thereof, and any pharmaceutically acceptable salts thereof. The molecular structures of ketamine and its enantiomers are shown below:

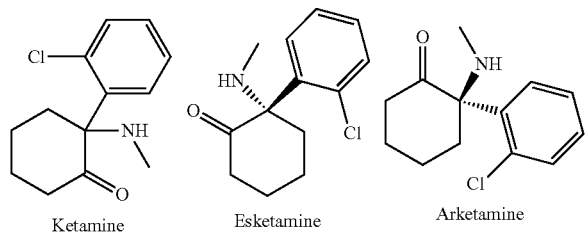

As generally understood, ketamine primarily functions to induce dissociative anesthesia by acting as a channel-blocking antagonist to the N-Methyl-D-aspartate (NMDA) receptor, an ion channel protein found in nerve cells. Ketamine acts to block the flow of ions through an open NDMA receptor that permits the transmission of electrical signals between the brain and the spinal column. This disruption of the NDMA receptor ultimately acts to block signals from reaching the conscious mind from other parts of the nervous system, which at sufficient dosages results in dissociation.

More recently, ketamine also has been recognized and studied for its antidepressant effects, especially in alleviating symptoms of major depressive disorder, treatment-resistant depression, and in reducing suicidal ideation which may arise due to a depression disorder or other mental disorder, such as posttraumatic stress disorder. Due to the relative recency of the recognition of Ketamine's antidepressant effects, the mechanism(s) of those effects are substantially less well understood relative to its dissociative mechanism, and are still a matter of ongoing investigation. Currently, investigate of ketamine as an antidepressant has only recently began entering the clinical stage.

A recent review by Zanos et al., *Mechanisms of ketamine action as an antidepressant*, Molecular Psychiatry (2018) 23, 801-811, discussed the various pre-clinical hypotheses regarding ketamine's mechanism of action as an antidepressant, and noted that a growing body of evidence suggested that while ketamine's NMDA inhibition is required for its antidepressant action, the key mechanism for ketamine's antidepressant action may be the targeting and activation of the mechanistic target of rapamycin (mTOR) signaling pathway, resulting in synaptogenesis in the prefrontal cortex, glycogen synthase kinase-3 beta (GSK-3β) inactivation, and enhanced expression of brain-derived neurotrophic factor (BDNF), an protein vital to the formation of long-term memory that acts to support survival of existing neurons and encourage growth and differentiation of new neurons and synapses. It was also noted that GSK-3β inhibitors such as lithium can enhance the efficacy of ketamine in this fashion and may prolong its antidepressant effect.

Clinical use of ketamine for the treatment of depression conditions and suicidal ideation has only recently begun in earnest. For example, a recent article in the American Journal of Psychiatry by Canuso et al, *Efficacy and Safety of Intranasal Esketamine for the Rapid Reduction of Symptoms of Depression and Suicidality in Patients at Imminent Risk for Suicide; Results of a Double-Blind, Randomized, Placebo-Controlled Study*, Am J Psychiatry, 2018 Jul. 1; 175(7); 620-630, observed, in a clinical setting, a significantly greater improvement in a patient's score on the Montgomery-Åsberg Depression Rating Scale (MADRS) at four hours and at 24 hours after intranasal administration of 84 mg of esketamine via an aerosol spray in addition to comprehensive treatment with standard antidepressants relative to comprehensive treatment with standard antidepressants alone. However, the study also noted significant side effects associate with the estketamine nasal spray protocol, and did not result in any significant reduction in MADRS score in the experimental group relative to the control group after 25 days.

Currently existing protocols for administration of ketamine to patients also do not result in completely desirable clinical outcomes. Current state of the art methods of ketamine treatments for depression typically display only around a 70% response rate in alleviating depression symptoms, which is considered to represent the industry standard.

Therefore, there is a need in the art for methods of treating patients suffering from conditions involving pain and depression via administration of ketamine, which do not suffer from the deficiencies associated with prior methods of treatment.

BRIEF SUMMARY

To solve these and other problems, a method of treating a patient having mental condition and/or pain in need of treatment is contemplated. According to an exemplary embodiment, this method comprises the administration to the patient of a first preparation comprising a pharmacologically effective amount of an antiemetic agent, and the administration to the patient of a second preparation, the second preparation comprising an intravenous infusion of a mixture of a pharmacologically effective amount of ketamine and a pharmacologically effective amount of a benzodiazepine.

The antiemetic agent of the first preparation may comprise at least one compound selected from the group comprising: non-selective 5-HT antagonist, 5-HT$_3$ receptor antagonist, 5-HT$_4$ receptor agonist, CB$_1$ agonist, D$_2$ receptor antagonist, D3 receptor antagonist, GABA receptor agonist, H$_1$ receptor antagonist, muscarinic acetylcholine receptor antagonist, NK$_1$ receptor antagonist, or combinations thereof. In the exemplary embodiment, the antiemetic agent comprises ondansetron.

In the second preparation, the benzodiazepine may be selected from the group comprising: 1,4-benzodiazepine, 1,5-benzodiazepine, 2,3-benzodiazepine, triazolobenzodiazepine, imidazobenzodiazepine, oxazolobenzodiazepine, thienodiazepine, thienotriazolodiazepine, thienobenzodiazepine, pyridodiazepine, pyridotriazolodiazepine, pyrralodiazepine, tetrahydroisoquinobenzodiazepine, benzodiazepine prodrug, or combinations thereof. In the exemplary embodiment, the benzodiazepine comprises lorazepam. The ratio of ketamine to benzodiazepine in the second preparation may be between 100:1 and 10:1 by weight. The second preparation may be administered as a saline solution.

According to one embodiment, the intravenous infusion of the second preparation additionally comprises a pharmaceutically effective amount of one or more of: an anesthetic, a sedative, an antiemetic, an anticonvulsant, an antidepressant, an antimigraine, an antipsychotic, an anxiolytic, or an antiparkinson. In a particular embodiment, the second preparation additionally comprises ondansetron.

According to a further embodiment, the method of treatment comprises the further administration to the patient of a third preparation, the third preparation comprising a pharmaceutically effective amount of an anti-inflammatory agent. According to a particular embodiment of this type, the third preparation comprises an intravenous infusion of ketorolac.

According to other embodiments, the method of treatment may comprise the administration to the patient of a third preparation, the third preparation being an intramuscular infusion comprising a pharmaceutically effective amount of a triptan. According to a particular embodiment of this type, the intramuscular infusion of the third preparation may comprise sumatriptan.

It is contemplated that the second preparation may be administered via continuous intravenous infusion at a rate of between 20 and 150 mg of ketamine per hour. It is also contemplated that the second preparation may be administered via continuous intravenous infusion at a rate of between 40 and 100 mg of ketamine per hour. The rate of administration to the patient may also be configured to vary during the period of administration. According to a particular embodiment, the second preparation may be delivered at a first rate of between 40-60 mg of ketamine per hour, subsequently delivered at a second rate of between 80-120 mg of ketamine per hour, and finally delivered at a third rate of about 25-35 mg of ketamine per hour. During the administration of the second preparation, at least 0.5 mg of ketamine may be delivered to the patient per kg of the patient's body mass. The administration of the intravenous infusion of the second preparation may also be performed over a time period of at least an hour.

DETAILED DESCRIPTION

According to various aspects of the present disclosure, new methods of treating depressive and/or pain conditions utilizing ketamine formulations are contemplated. In one embodiment, a series of infusions are given to a patient. In a second embodiment, a patient may self-administer a series or intranasal administrations.

According to one exemplary version of the first embodiment including the series of infusions, a first preparation is administered and contains an antiemetic agent, with 4 mg of ondansetron administered via intravenous infusion being preferred, and a second preparation is subsequently administered, the second preparation being an intravenous infusion containing a mixture of ketamine and a benzodiazepine, with a 30 ml saline solution containing 100 mg of ketamine and 2 mg of lorazepam being preferred. The second preparation is delivered to the patient via continuous intravenous infusion over a period of about an hour, at a first rate of delivery of around 15 ml/hour, subsequently elevated to a second rate of delivery of around 30 ml/hour, and finally reduced to a third rate of delivery of around 10 ml/hour. According to various refinements, the second preparation may optionally contain additional ondansetron, greater amounts of lorazepam, or other variations, and subsequent infusion may also be delivered to the patient. For example, in a specific embodiment, it is contemplated that an intramuscular infusion containing between 15-30 mg of sumatriptan is administered to the patient.

As used herein, for avoidance of confusion, references to general and specific pharmaceutical compounds or preparations will be understood to interchangeably refer to any and all pharmaceutically active forms or preparations of those compounds, including but not limited to different enantiomers or enantiomeric proportions, or pharmaceutically acceptable salts thereof, or in a protonated or free base form, or prodrugs thereof.

Ondansetron is an antimetic medication sold under the trade names Zofran and Ondisolv in various markets. Ondansetron is a 5-HT$_3$ receptor antagonist (a "setron") generally used in controlling nausea and vomiting in postoperative conditions and in chemotherapy patients, and well as for various off-label uses. 5-HT$_3$ receptor antagonists bind to and block the 5-HT$_3$ receptor, which is a ligand-gated ion channel found in the vagus nerve and in the area postrema. Synaptic transmission initiated via the 5-HT$_3$ receptor directly mediates the nausea and vomiting reflex. Ondansetron has the following molecular structure:

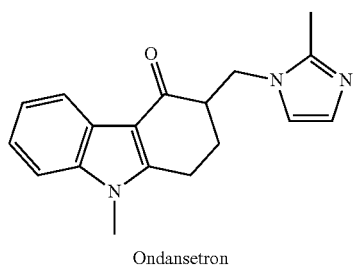 [SMILES: Cc1nccn1CC1CCc2c(c3ccccc3n2C)C1=O]

Ondansetron

According to the presently contemplated method of treating a patient, a first preparation comprising a pharmacologically effective amount of an antiemetic agent is administered to the patient. In the exemplary embodiment, the first preparation comprises a 4 mg intravenous infusion of ondansetron. However, it may be seen that in other embodiments, other preparations may be administered to the patient which may vary from this exemplary embodiment. For example, other methods of delivery than intravenous infusion may be utilized, including but not limited to oral delivery, transmucosal (e.g. nasal, buccal, sublingual, vaginal, ocular, rectal, etc.) delivery, inhalatory delivery, intramuscular injection, and any other form of delivery which may achieve administration to the patient of a pharmaceutically effective amount of the antiemetic agent. Likewise, it may also be seen that other antiemetic agents than ondansetron may be utilized, including but not limited to other setrons, or other antiemetic compounds or preparations, including but not limited to other 5-$HT_3$ receptor antagonist, non-selective 5-HT antagonists, 5-$HT_4$ receptor agonists, $CB_1$ agonists, $D_2$ receptor antagonists, D3 receptor antagonists, GABA receptor agonists, $H_1$ receptor antagonists, muscarinic acetylcholine receptor antagonists, $NK_1$ receptor antagonists, or combinations thereof.

Lorazepam is a benzodiazepine medication sold under various trade names including Ativan, Almazine, and Tavor. Lorazepam has various properties, including acting as a sedative, a hypnotic, an amnesiac, and an anxiolytic. Like other benzodiazepines, Lorazepam is generally understood to act primarily by enhancing the effect of gamma-aminobutyric acid (GABA) at the GABAA receptor. As the primary inhibitory neurotransmitter, GABA acts to reduce neuronal excitability throughout the nervous system. Compared to other benzodiazepines such as diazepam (valium), lorazepam is substantially more potent and longer acting. Lorazepam has the following molecular structure:

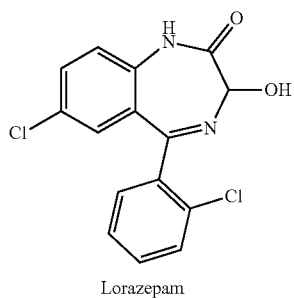 [SMILES: O=C1Nc2ccc(Cl)cc2C(c2ccccc2Cl)=NC1O]

Lorazepam

It may be seen however that other benzodiazepines may be utilized. Such other benzodiazepines may be, for example but without limitation, a 1,4-benzodiazepine, a 1,5-benzodiazepine, a 2,3-benzodiazepine, a triazolobenzodiazepine, an imidazobenzodiazepine, an oxazolobenzodiazepine, a thienodiazepine, a thienotriazolodiazepine, a thienobenzodiazepine, a pyridodiazepine, a pyridotriazolodiazepine, a pyrralodiazepine, a tetrahydroisoquinobenzodiazepine, a benzodiazepine prodrug, or combinations thereof.

According to the presently contemplated method of treating a patient, a second preparation is administered, the second preparation being an intravenous infusion comprising a mixture of a pharmacologically effective amount of ketamine and a pharmacologically effective amount of a benzodiazepine. In the exemplary embodiment, the second preparation may comprise a solution of ketamine and lorazepam in a ratio of 50:1 by weight. Specifically, such a solution may be formulated as a 30 ml saline solution containing 100 mg (~3.33 mg/cc) of ketamine and 2 mg (~0.07 mg/cc) of lorazepam. However, in other embodiments, it may be seen that other benzodiazepines than lorazepam may be utilized, such as diazepam, midazolam, alprazolam, temazepam, clonazepam, among others. Likewise, it may be seen that the amount of lorazepam or other benzodiazepine may be varied. For example, in other contemplated embodiments, it is envisioned that the ratio of ketamine to lorazepam utilized in intravenous infusion of the second preparation may be anywhere from between 100:1 and 10:1 by weight.

It has been observed that following administration of the first preparation of a pharmaceutically effective amount of an antiemetic agent, the administration of the solution of the second preparation, when delivered to the patient via continuous intravenous infusion over a period of time of around an hour or more, at a rate of between 25 to 150 mg of ketamine an hour, results in the effective treatment of a patient's depression and/or pain conditions with a greater response rate and with reduced side-effects relative to conventional treatment techniques utilizing ketamine. It is thought that these benefits result from the co-administration of ketamine and benzodiazepine in combination with a potent antiemetic.

It has been found that the rate of administration of the second preparation is important in realizing such an effective treatment. Specifically, in the exemplary embodiment, delivery of the second preparation is via continuous intravenous infusion for a time period of at least an hour, at an overall rate of administration of between 25 and 150 mg of ketamine per hour, with a proportional administration of lorazepam, and preferably at an overall rate of between 40 and 100 mg of ketamine per hour. More particularly, it has been found that by administering the intravenous infusion with a varying rate of delivery over the time period during which it is administered, the response rate of patients may be maximized with harmful side effects minimized. The preferred variation in the rate of delivery takes the shape of a bell curve, with an initial first rate of delivery of between 40-60 mg of ketamine per hour, a second rate of delivery, where the amount delivered is maximized, of between 90-110 mg of ketamine per hour, and a final third rate of delivery of about 20-40 mg of ketamine per hour, all with proportionally similar rates of delivery of the co-administered lorazepam. However, it may be seen that in other embodiments, other rates of delivery or variations in rates of delivery of the second preparation may be utilized. For example, it may be seen that it may be preferred to vary the overall amount of ketamine delivered in proportion with the patient's needs, and that it may be desirable to deliver at least 0.5 mg of ketamine to the patient per kg of the patient's body mass.

A variety of more specific embodiments of the presently disclosed methods of treatment have been developed to treat specific conditions in addition to or as an alternative to general depression conditions. According to one particular embodiment configured for treatment of depression and mental health conditions, the second preparation may comprise a 30 ml saline solution containing 100 mg of ketamine and 4 mg of lorazepam. According to another particular embodiment configured for treatment of migraine and headache pain, the second preparation may be a 32 ml saline solution comprising 100 mg of ketamine, 4 mg of lorazepam, and 4 mg of ondansetron, and a third preparation may be administered comprising an intramuscular injection of a triptan, and specifically between 4 and 6 mg of sumatriptan. According to another particular embodiment configured for treatment of cancer-related pain and depression, the first preparation may be 8 mg of ondansetron. According to a further particular embodiment configured for treatment of inflammation, a third preparation may be administered comprising an intravenous infusion of between 15 and 30 mg of ketorolac.

Disease conditions for which the presently contemplated methods of treatment may be effective to treat include, for example but without limitation, ADHD, ALS, amyotrophic lateral sclerosis, anxiety, arachnoiditis, arthritic pain, autism, bipolar disorder, cancer pain, chronic fatigue syndrome, chronic pain, chronic pelvic pain, CPS or CRPS 1 and 2, depression, endometriosis, fibromyalgia, gastroparesis, glutamate storm also known as post concussive syndrome, headaches/migraines, inflammatory bowel disease, inflammatory pain, insomnia, lupus, Lyme disease, major depressive disorder (clinical depression), Ménière's disease, multiple sclerosis, musculoskeletal pain, neuropathic pain, obsessive-compulsive disorder, osteoarthritis, osteoporosis, Parkinson's disease, Pott's syndrome, PTSD, Raynaud syndrome, repetitive stress disorder, Sjögren syndrome, substance use disorder, and suicidal ideation.

In the second embodiment, a patient may self-administer the medication. For example, a first preparation may be administered and contains an antiemetic agent, with 4 mg of ondansetron administered via an intranasal spray or an oral dissolvable tablet (ODT) of 4 mg of ondansetron.

The patient may further self-administer the second preparation. The intranasal spray may contain a mixture of ketamine and a benzodiazepine, with 25 mg of ketamine and 0.5 mg of lorazepam being preferred. However, the precise dosage will depend on various factors, including the age, and body mass. Thus, the ketamine may be administered in a range of 25 mg to 200 mg, with a range of 25 mg to 150 mg being more preferred, and a range of 25 mg to 100 mg being most preferred. The benzodiaszepine would increase linearly with the ketamine dosage, for example 50 mg of ketamine would be accompanied by 1 mg of, for example, lorazepam. 75 mg of ketamine would be accompanied by 1.5 mg of, for example, lorazepam. And, 100 mg of ketamine would be accompanied by 2 mg of, for example, lorazepam.

The ketamine and the benzodiazepine may be mixed in to form a single pharmaceutical compound. The spray device may administer a quantum of the smallest dose. For example, with each actuation of the spray device, 25 mg of ketamine and 0.5 mg of lorazepam may be administered. Thus, if the dose is 75 mg of ketamine and 1.5 mg of lorazepam, the patient will self-administer three sprays from the spray device. Alternatively, the ketamine and the benzodiazepine may be administered from separate spray devices.

The doses are administered twice weekly. For example, one dose may be administered on a Monday, and a second dose on a Thursday. The days may be shifted to any of the days of the week, but the goal is to even out the amount of pharmaceutical in the patient's system as much as possible. Thus, the doses are administered every three or four days. Doses may continue to be administered as long as symptoms persist. Further, dosages may be changed after the initial or subsequent doses based on the efficacy of the dose. Further, the pharmaceutical compound may be changed based on efficacy of the dose, or changing symptoms as discussed further below.

As with the above disclosure of the first embodiment, various other pharmaceuticals may be added to treat predetermined conditions. These, too may be mixed with the ketamine and other pharmaceuticals for form a single compound administered from a single spray device or may be administered from separate devices.

Experimental Results

In a first study, patients were assessed based upon Beck's Depression Inventory (BDI) before the first treatment and after each instance of treatment according to the presently contemplated synergistic method. A significant (p<0.001) change between the pre-administration BDI score and mean of each patient's post-administration (for the first and all subsequent administrations) BDI score was observed, with the average observed change in patients having substantially more effect for patients falling into more severe BDI categories. Results are reported in the following tables:

TABLE 1

Change in BDI following administration

| BDI Category | Pre First Infusion Mean | N | Post Infusion Mean | Change |
|---|---|---|---|---|
| All | 19.6 ± 13.2 | 217 | 16.6 ± 11.8 | −3.0 |
| Minimal | 6.6 ± 4.0 | 84 | 5.7 ± 4.0 | −0.9 |
| Mild | 16.7 ± 1.7 | 35 | 15.3 ± 5.1 | −1.4 |
| Moderate | 24.3 ± 2.9 | 41 | 20.8 ± 5.4 | −3.5 |
| Severe | 37.3 ± 7.0 | 57 | 30.3 ± 9.6 | −7.0 |

TABLE 2

Movement of patients between BDI categories following administration

| BDI Category | Pre First Infusion | Lower Category | Higher Category | Post Distribution |
|---|---|---|---|---|
| Minimal | 84 | 0 | 5 | (79, 5, 0, 0) |
| Mild | 35 | 12 | 5 | (12, 15, 4, 1) |
| Moderate | 41 | 18 | 3 | (3, 15, 20, 3) |
| Severe | 57 | 23 | 0 | (3, 5, 15, 34) |

TABLE 3

BDI Contingency Table showing movement of patients following second and subsequent infusions

| | | Post Infusion BDI Category | | | |
|---|---|---|---|---|---|
| | | Minimal | Mild | Moderate | Severe |
| Pre Infusion BDI Category | Minimal | 79 | 5 | 0 | 0 |
| | Mild | 12 | 18 | 4 | 1 |
| | Moderate | 3 | 15 | 20 | 3 |
| | Severe | 3 | 5 | 15 | 24 |

In a second study, 339 patients who received more than one administration of the presently contemplated synergistic treatment method self-reported whether their treated condition(s) benefited following treatment. On average, each patient received between 5 and 6 treatments, with a total of around 2000 treatments administered. Overall, out of those 339 patients 309 reported a benefit to their treated condition(s) after 1 or 2 treatments (91.15%), and 294 reported an overall benefit to their treated symptoms at the end of their full treatment regimen (86.73%). An overall breakdown of the results is shown by the table below:

TABLE 4

Patient Reported Benefits after Short Term and Extended Treatments

| Treated Condition | N | Reported Benefit after 1-2 treatments | % | Reported Benefit at End of Treatments | % |
|---|---|---|---|---|---|
| All | 339 | 309 | 91.15% | 294 | 86.73% |
| Depression | 166 | 153 | 92% | 146 | 88% |
| Anxiety | 109 | 102 | 94% | 98 | 90% |
| PTSD | 47 | 46 | 98% | 43 | 91% |
| Fibromyalgia | 63 | 63 | 100% | 58 | 92% |
| Chronic Pain | 88 | 80 | 91% | 74 | 84% |
| Neuropathy | 124 | 115 | 93% | 110 | 89% |
| Headaches/Migraine | 64 | 59 | 92% | 60 | 94% |
| Musculoskeletal Pain | 127 | 111 | 87% | 109 | 86% |

As may be seen, of those 339 patients, 166 complained of depression, with 153 reporting a benefit after 1-2 treatments (92%), and 146 reporting a benefit at the end of their full treatment regimen (88%). 109 patients complained of anxiety, with 102 reporting a benefit after 1-2 treatments (94%), and 98 reporting a benefit at the end of their full treatment regimen (90%). 47 patients complained of PTSD, with 46 patients reporting a benefit after 1-2 treatments (98%), and 43 reporting a benefit at the end of their full treatment regimen (91%). 63 patients complained of fibromyalgia, with 63 patients reporting a benefit after 1-2 treatments (100%), and 58 reporting a benefit at the end of their full treatment regimen (92%). 88 patients complained of chronic pain, with 80 patients reporting a benefit after 1-2 treatments (91%), and 74 patients reporting a benefit at the end of their full treatment regimen (84%). 124 patients complained of neuropathy, with 115 patients reporting a benefit after 1-2 treatments (93%), and 110 patients reporting a benefit at the end of their full treatment regimen (89%). 64 patients complained of headaches or migraines, with 59 patients reporting a benefit after 1-2 treatments (92%), and 60 patients reporting a benefit at the end of their full treatment regimen (94%). 127 patients complained of musculoskeletal type pain, with 111 patients reporting a benefit after 1-2 treatments (87%), and 109 patients reporting a benefit at the end of their full treatment regimen (86%). It may therefore be seen that the presently contemplated methods may display substantially better outcomes to patients relative to the present 70% response rate in alleviating depression symptoms considered to represent the industry standard, and may display substantially better outcomes in alleviating other symptoms. Similar to other studies, treatment with ketamine displays a higher short-term efficacy with some diminishment in efficacy after extended treatment, but substantial long-term effects were realized as well via the presently contemplated methods of treatment.

Patients in the second study were also evaluated based upon self-reported need or use of medication prior to treatment, after 1-2 treatments, and at the end of treatment. Results are shown in the table below:

TABLE 5

Patients Reported Medication Use after Short Term and Extended Treatments

| Medication | N | Reduced Need after 1-2 Treatments | % | Reduced Need after End of Treatments | % |
|---|---|---|---|---|---|
| Pain | 276 | 64 | 23% | 115 | 42% |
| Mental Health | 211 | 28 | 13% | 57 | 27% |

As may be seen, 276 patients in the second study reported a need or use of pain medication to treat their complained-of conditions, with 115 patients reporting an overall decrease in their need or use of pain medication at the conclusion of their treatment regimen (42%). Of those 115 patients, 64 reported a decrease in their need/use of pain medication after only 1-2 treatments (23%). 211 patients in the second study reported a need or use of a behavioral health medication to treat their complained-of conditions, with 57 patients reporting an overall decrease in their need or use of behavior health medication at the conclusion of their treatment regimen (27%). Out of those 57 patients, 28 reported a decrease in their need/use of behavioral health medication after only 1-2 treatments (13.0%).

Patients also reported the experience of any adverse side effects following each instance of treatment. Results of reports of side effects are shown in the table below:

TABLE 6

Reported Instance of Side Effects

| Side Effect Type | Reported Instance of Side Effects | % |
|---|---|---|
| Any | 163 | 8% |
| Nausea | 94 | 5% |
| Anxiety | 77 | 4% |

As may be seen by Table 6, out of the nearly 2000 treatments administered among the 339 patients, 163 instances of side effects were reported (8%), with 94 instances of nausea reported (5%) and 77 instances of anxiety reported (4%). Four of these instances involved patients reporting of both nausea and anxiety.

It may therefore be seen the presently contemplated methods may not only display substantially improved results relative to the industry norm, but may also reduce the need for other medications for patients suffering from depression and pain. This may result in beneficial outcomes, especially for patients reliant on opioids or other medications which may have potential for addiction or other negative outcomes.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the exemplary embodiments.

What is claimed is:

1. A method of treating a patient having depression in need of treatment, the method comprising:
   administering to the patient a first preparation, the first preparation comprising a pharmacologically effective amount of an antiemetic agent; and administering to the patient a second preparation, the second preparation being an intravenous infusion comprising a mixture of a pharmacologically effective amount of ketamine and a pharmacologically effective amount of a benzodiazepine.

2. The method of claim 1, wherein the antiemetic agent of the first preparation comprises at least one compound selected from the group consisting of non-selective 5-HT antagonist, $5-HT_3$ receptor antagonist, $5-HT_4$ receptor agonist, $CB_1$ agonist, $D_2$ receptor antagonist, $D_3$ receptor antagonist, GABA receptor agonist, $H_1$ receptor antagonist, muscarinic acetylcholine receptor antagonist, $NK_1$ receptor antagonist, or combinations thereof.

3. The method of claim 2, wherein the first preparation comprises an intravenous infusion of ondansetron.

4. The method of claim 1, wherein in the second preparation, the benzodiazepine is selected from the group consisting of 1,4-benzodiazepine, 1,5-benzodiazepine, 2,3-benzodiazepine, triazolobenzodiazepine, imidazobenzodiazepine, oxazolobenzodiazepine, thienodiazepine, thienotriazolodiazepine, thienobenzodiazepine, pyridodiazepine, pyridotriazolodiazepine, pyrralodiazepine, tetrahydroisoquinobenzodiazepine, a benzodiazepine prodrug, or combinations thereof.

5. The method of claim 4, wherein the benzodiazepine is lorazepam.

6. The method of claim 1, wherein in the second preparation, the ratio of ketamine to benzodiazepine is between 100:1 and 10:1 by weight.

7. The method of claim 1, wherein the second preparation is administered as a saline solution.

8. The method of claim 1, wherein the second preparation additionally comprises a pharmacologically effective amount of one or more of: an anesthetic, a sedative, an antiemetic, an anticonvulsant, an antidepressant, an antimigraine, an antipsychotic, an anxiolytic, an antiparkinson.

9. The method of claim 8, wherein the second preparation additionally comprises ondansetron.

10. The method of claim 1, further comprising administering to the patient a third preparation, the third preparation comprising a pharmaceutically effective amount of an anti-inflammatory agent.

11. The method of claim 10, wherein the third preparation comprises an intravenous infusion of ketorolac.

12. The method of claim 10, wherein the third preparation comprises an intramuscular infusion of a pharmaceutically effective amount of a triptan.

13. The method of claim 12, wherein the third preparation comprises sumatriptan.

14. The method of claim 1, wherein the second preparation is administered via continuous intravenous infusion at a rate of between 20 and 150 mg of ketamine per hour.

15. The method of claim 1, wherein the second preparation is administered via continuous intravenous infusion at a rate of between 40 and 100 mg of ketamine per hour.

16. The method of claim 14, wherein the rate of administration of the second preparation is configured to vary during the period of administration.

17. The method of claim 16, wherein the second preparation is initially delivered at a first rate of between 40-60 mg of ketamine per hour, subsequently delivered at a second rate of between 80-120 mg of ketamine per hour, and finally delivered at a third rate of about 20-40 mg of ketamine per hour.

18. The method of claim 1, wherein during the administration of the second preparation, at least about 0.5 mg of ketamine is delivered to the patient per kg of the patient's body mass.

19. The method of claim 1, wherein the administration of the second preparation is performed over a time period of at least an hour.

20. The method of claim 1, wherein the patient has major depressive disorder.

21. The method of claim 1, wherein
    (i) the first preparation comprises an intravenous infusion of ondansetron;
    (ii) in the second preparation the benzodiazepine is lorazepam; and
    (iii) in the second preparation, the ratio of ketamine to benzodiazepine is between 100:1 and 10:1 by weight.

22. The method of claim 21, wherein in the second preparation, the ratio of ketamine to benzodiazepine is 50:1 by weight.

23. The method of claim 22, wherein the second preparation is administered via continuous intravenous infusion at a rate of between 40 and 100 mg of ketamine per hour.

24. The method of claim 23, wherein the patient has major depressive disorder.

25. The method of claim 23, wherein the first preparation comprises an intravenous infusion of 4 mg of ondansetron.

26. A method of treating depression in a patient in need thereof, the method comprising concurrently administering to the patient:
    (i) a pharmacologically effective amount of an antiemetic agent;
    (ii) a pharmacologically effective amount of ketamine; and
    (iii) a pharmacologically effective amount of a benzodiazepine.

27. The method of claim 26, wherein the administering is by intravenous infusion of a mixture of the antiemetic agent, the ketamine, and the benzodiazepine, wherein the ratio of ketamine to benzodiazepine is between 100:1 and 10:1 by weight.

28. The method of claim 27, wherein the antiemetic agent is ondansetron and the benzodiazepine is lorazepam.

29. The method of claim 28, wherein the intravenous infusion is administered at a rate of between 20 and 150 mg of ketamine per hour.

30. The method of claim 29, wherein the patient has major depressive disorder.

* * * * *